(12) United States Patent
Kristanto et al.

(10) Patent No.: US 11,510,587 B2
(45) Date of Patent: Nov. 29, 2022

(54) LEFT VENTRICLE SEGMENTATION IN CONTRAST-ENHANCED CINE MRI DATASETS

(71) Applicant: Pie Medical Imaging B.V., Maastricht (NL)

(72) Inventors: Wisnumurti Kristanto, Maastricht (NL); Jean-Paul Aben, Limbricht (NL)

(73) Assignee: Pie Medical Imaging B.V., Maastricht (NL)

( * ) Notice: Subject to any disclaimer, the term of this patent is extended or adjusted under 35 U.S.C. 154(b) by 605 days.

(21) Appl. No.: 16/167,152

(22) Filed: Oct. 22, 2018

(65) Prior Publication Data

US 2019/0125206 A1    May 2, 2019

(30) Foreign Application Priority Data

Oct. 31, 2017    (EP) .................................... 17199310

(51) Int. Cl.
 *G06K 9/00* (2022.01)
 *A61B 5/055* (2006.01)
 (Continued)

(52) U.S. Cl.
 CPC .......... *A61B 5/055* (2013.01); *G01R 33/5608* (2013.01); *G06T 7/0012* (2013.01); *G06T 7/11* (2017.01); *G06T 7/174* (2017.01); *G06V 10/26* (2022.01); *G06V 10/755* (2022.01); *A61B 2576/023* (2013.01); *G01R 33/5601* (2013.01); *G01R 33/56325* (2013.01); *G06T 7/136* (2017.01); *G06T 7/149* (2017.01); *G06T 2200/04* (2013.01); *G06T 2207/10081* (2013.01); *G06T 2207/10088* (2013.01);
 (Continued)

(58) Field of Classification Search
 CPC ...................................................... G06T 7/174
 See application file for complete search history.

(56) References Cited

U.S. PATENT DOCUMENTS

| 6,252,402 B1 | 6/2001 | Sanfilippo et al. |
| 7,332,912 B2 | 2/2008 | Pittaluga et al. |
| (Continued) | | |

FOREIGN PATENT DOCUMENTS

WO    WO2015010745 A1    1/2015

OTHER PUBLICATIONS

"Accurate and Objective Infarct Sizing by Contrast-Enhanced Magnetic Resonance Imaging in a Canine Myocardial Infarction Model", Amado, et al., Journal of the American College of Cardiology, vol. 44, No. 12, pp. 2383-2389, 2004.
(Continued)

*Primary Examiner* — Oneal R Mistry
(74) *Attorney, Agent, or Firm* — Gordon & Jacobson, P.C.

(57) ABSTRACT

A method for delineating a ventricle from MRI data relating to the heart of a patient, the method comprising:
 a) providing a contrast-enhanced cine MRI dataset;
 b) providing one or more additional MRI datasets;
 c) segmenting one or more features on the additional MRI dataset or datasets;
 d) mapping the segmented features to the contrast-enhanced cine MRI dataset; and
 e) using the segmented features as mapped in step d) to assist segmentation of the ventricle on the contrast-enhanced cine MRI dataset.
A corresponding device and computer program are also disclosed.

23 Claims, 9 Drawing Sheets

(51) Int. Cl.
| | |
|---|---|
| G06T 7/00 | (2017.01) |
| G06T 7/174 | (2017.01) |
| G06T 7/11 | (2017.01) |
| G01R 33/56 | (2006.01) |
| G06V 10/26 | (2022.01) |
| G06V 10/75 | (2022.01) |
| G06T 7/136 | (2017.01) |
| G06T 7/149 | (2017.01) |
| G01R 33/563 | (2006.01) |

(52) U.S. Cl.
CPC ............... *G06T 2207/20048* (2013.01); *G06T 2207/20116* (2013.01); *G06T 2207/30048* (2013.01)

(56) References Cited

U.S. PATENT DOCUMENTS

| | | | |
|---|---|---|---|
| 7,864,997 B2 | 1/2011 | Aben | |
| 2004/0132006 A1* | 7/2004 | O'Donnell | G06T 7/0012 435/4 |
| 2006/0253017 A1 | 11/2006 | O'Donnell et al. | |
| 2009/0290778 A1 | 11/2009 | Sun et al. | |
| 2012/0121154 A1 | 5/2012 | Xue et al. | |
| 2014/0071125 A1* | 3/2014 | Burlina | G06T 17/00 345/420 |
| 2016/0098833 A1* | 4/2016 | Tsadok | G06K 9/6201 382/128 |
| 2016/0140751 A1* | 5/2016 | Jafarkhani | A61B 8/466 382/131 |
| 2016/0314581 A1* | 10/2016 | Contini | G06T 7/248 |
| 2017/0109881 A1* | 4/2017 | Avendi | G06T 7/149 |
| 2018/0078312 A1* | 3/2018 | Trayanova | G06T 17/00 |

OTHER PUBLICATIONS

"Active Appearance Models", T.F. Cootes, et al, Proc European Conference on Computer Vision 1998, vol. 2, pp. 484-198, 1998.
"A review of segmentation methods in short axis cardiac MR images", C. Petitjean and J.N. Dacher, Medical Image Analysis, vol. 15, No. 2, 2011.
"A Threshold Selection Method from Gray-Level Histograms", N. Otsu, IEEE Transactions on Systems, Man, and Cybernetics, vol. SMC-9, No. 1, pp. 62-66, 1979.
"Accuracy of contrast-enhanced cine-MR sequences in the assessment of left ventricular function: comparison with precontrast cine-MR sequences, Results of a bicentric study", J.C. Lasalarie, et al, European Radiology, vol. 17, No. 11, pp. 2838-2844, 2007.
"Automated quantification of myocardial infarction using graph cuts on contrast delayed enhanced magnetic resonance images", Y. Lu, et al, Quantitative Imaging in Medicine and Surgery, vol. 2, No. 2, pp. 81-86, 2012.
"Automatic Localization OF Anatomical Landmarks in Cardiac MR Perfusion Using Random Forests", Kim Youn-Chul et al., Biomedical Signal Processing and Control, vol. 38, Jul. 28, 2017, pp. 370-378, XP085160095.
"Automatic segmentation of myocardium at risk from contrast-enhanced SSFP CMR: validation against expert readers and SPECT", J. Tufvesson, et al, BMC Medical Imaging, vol. 16, No. 19, 2016.

"Dark blood late enhancement imaging", Peter Kellman et al., Journal of Cardiovascular Magnetic Resonance, 2016, 18:77.
European Search Report dated Apr. 27, 2018 of EP1719310.
"First-Pass Cardiac Perfusion: Evaluation with Ultrafast MR Imaging", D.J. Atkinson, et al, Radiology, vol. 174, No. 3, pp. 757-762, 1990.
Fully Automated Framework for the Analysis of Myocardial First-Pass Perfusion MR Images, Beache Garth M et al., Medical Physics, vol. 41, No. 10, Sep. 24, 2014, XP012190233.
"Functional Cardiac MR Imaging with Steady-State Free Precision (SSFP) Significantly Improves Endocardial Border Delineation Without Contrast Agents", H. Thiele, et al Journal of Magnetic Resonance Imaging, vol. 24, No. 4, pp. 362-367, 2001.
"Fuzzy Connectedness and Object Definition: Theory, Algorithms, and Applications in Image Segmentation", J.K. Udupa and S. Samarasekera, Graphical Models and Image Processing, vol. 23, No. 3, pp. 246-261, 1996.
"Microvascular obstruction and myocardial function after acute myocardial infarction: assessment by using contrast-enhanced cine MR imaging", G.L. Raff, et al., Radiology, vol. 340, No. 2, pp. 529-536, 2006.
"MRI Based Quantification of Myocardial Perfusion at Rest and Stress Using Automated Frame-by-Frame Segmentation and Non-Rigid Registration", Tarroni G et al., Computers in Cardiology, 2010, IEEE, Sep. 26, 2010, pp. 1-4, XP032008208.
"Multimodality Image Registration by Maximization of Mutual Information", F. Maes, et al., IEEE Transactions on Medical Imaging, vol. 16, No. 2, pp. 187-198, 1997.
"Multiseeded Segmentation Using Fuzzy Connectedness", Gabor T. Herman and Bruno M. Carvalho, IEEE Transactions on Pattern Analysis and Machine Intelligence, vol. 23, No. 5, pp. 460-474, 2001.
"Myocardial Segmentation of Late Gadolinium Enhanced MR Images by Propagation of Contours from Cine MR Images", Wei Dong et al, ECCV 2016 Conference, Springer International Publishing, Cham, pp. 428-435, XP047463458.
"Myocardial tissue characterization by magnetic resonance imaging: novel applications of T1 and T2 mapping", Ferreira et al., J Thorac Imaging. May 2014;29(3):147-54.
"Reproducibility of MRI Measurements of Right Ventricular Size and Function in Patients with Normal and Dilated Ventricles", C.F. Mooij, et al., Journal of Magnetic Resonance Imaging, vol. 28, No. 1, pp. 67-73, 2008.
"Snakes: Active Contour Models", M. Kass, et al., International Journal of Computer Vision, vol. 1, No. 4, pp. 321-331, 1998.
"Time elapsed after contrast injection is crucial to determine infarct transmurality and myocardial functional recovery after an acute myocardial infarction", J.F. Rodriguez-Palomares, et al. Journal of Cardiovascular Magnetic Resonance, vol. 17, No. 1, pp. 43, 2015.
"Value of Contrast-Enhanced, Balanced Cine-MR Sequences in the Assessment of Apparent Infarct Size After Acute Myocardial Infarction: A Prospective Comparison With Delayed-Enhancement Sequences", J-P. Laissy, et al., Journal of Magnetic Resonance Imaging, vol. 22, No. 6, pp. 765-771, 2005.
"Value of Gadolinium-Diethylene-Triamine Pentaacetic Acid Dynamics in Magnetic Resonance Imaging of Acute Myocardial Infarction with Occluded and Reperfused Coronary Arteries After Thrombolysis", A.C. Van Rossum, et al., The American Journal of Cardiology, vol. 65, No. 13, pp. 845-851, 1990.

\* cited by examiner

LEFT VENTRICLE SEGMENTATION IN CONTRAST-ENHANCED CINE MRI DATASETS

CROSS-REFERENCE TO RELATED APPLICATIONS

The present application claims priority from EP17199310, filed on Oct. 31, 2017, entitled "IMPROVING LEFT VENTRICLE SEGMENTATION IN CONTRAST-ENHANCED CINE MRI DATASETS," herein incorporated by reference in its entirety.

BACKGROUND

1. Field

The present application relates to medical image segmentation, and more particularly to segmentation of an anatomical structure in a medical image.

2. State of The Art

Magnetic resonance imaging (MRI) has been the preferred imaging modality to assess heart condition. A wealth of information about the heart can be obtained with various MRI imaging sequence within one imaging session, for instance a cine MRI to assess morphological and functional performance of the heart, a first-pass perfusion MRI to assess blood intake of the myocardial tissue, a delayed-enhancement MRI to assess damaged myocardial tissue, and a tissue mapping sequence to characterize each tissue based on their relaxation time.

Cine MRI acquires images covering the whole heart in multiple thin slices over the complete cardiac cycle. Therefore, the anatomical structure of the heart, such as wall thickness and any abnormality can be examined. The movement of the myocardium performing its main function to pump the blood can also be thoroughly examined to recognize any anomalies.

Some MRI acquisitions need contrast agent to be administered to the patient to highlight certain features of the heart. The most commonly used MRI contrast agent for contrast enhancement are gadolinium-based. Traditionally, cine MRI datasets are acquired prior to contrast administration to acquire a visualization with a good differentiation between blood-pool cavity and the surrounding myocardium without any contrast enhancement as for instance taught by H. Thiele, et al in "Functional Cardiac MR Imaging With Steady—State Free Precision (SSFP) Significantly Improves Endocardial Border Delineation Without Contrast Agents", Journal of Magnetic Resonance Imaging, vol. 24, no. 4, pp. 362-367, 2001.

After contrast administration to the patient, some image acquisitions require a waiting time up to 30 minutes before they can be performed as for instance taught by J. F. Rodriguez-Palomares, et al in "Time elapsed after contrast injection is crucial to determine infarct transmurality and myocardial functional recovery after an acute myocardial infarction", Journal of Cardiovascular Magnetic Resonance, vol. 17, no. 1, pp. 43, 2015.

A recent development, as for instance taught by G. L. Raff, et al in "Microvascular obstruction and myocardial function after acute myocardial infarction: assessment by using contrast-enhanced cine MR imaging", Radiology, vol. 340, no. 2, pp. 529-536, 2006, suggests cine MRI to be performed after contrast administration during the waiting moment to save time and reduce discomfort level of the patient, while still maintaining its performance in facilitating morphological and functional analysis of the heart. This approach is called contrast-enhanced cine MRI.

The analysis of MRI images requires segmentation of the ventricle, for instance in the form of segmentation of the inner border (also known as the endocardial border or the border between the blood-pool cavity and the myocardium), or the outer border (also known as the epicardial border). A manual segmentation of the ventricle is a tedious task, requiring up to 54 minutes as reported by C. F. Mooij, et al in "Reproducibility of MRI Measurements of Right Ventricular Size and Function in Patients with Normal and Dilated Ventricles", Journal of Magnetic Resonance Imaging, vol. 28, no. 1, pp. 67-73, 2008.

An automatic segmentation method might help the clinician in producing an accurate, time-saving and reproducible measurement. Numerous automatic segmentation methods, for instance based on deformable models or image-based, methods have been developed to segment ventricular borders at cine MRI as taught by C. Petitjean and J-N. Dacher in "A review of segmentation methods in short axis cardiac MR images", Medical Image Analysis, vol. 15, no. 2, 2011.

However, contrast-enhanced cine MRI poses difficulty challenge for the ventricle segmentation. Due to the contrast uptake by the myocardium and especially the infarcted myocardium, their signal intensity increases (also known as hyper-enhancement) so that the contrast or difference with the signal intensity of the blood-pool cavity decreases, as for instance taught by J-P. Laissy, et al in "Value of Contrast-Enhanced, Balanced Cine-MR Sequences in the Assessment of Apparent Infarct Size After Acute Myocardial Infarction: A Prospective Comparison With Delayed-Enhancement Sequences", Journal of Magnetic Resonance Imaging, vol. 22, no. 6, pp. 765-771, 2005.

As reported by J-C. Lasalarie, et al in "Accuracy of contrast-enhanced cine-MR sequences in the assessment of left ventricular function: comparison with precontrast cine-MR sequences. Results of a bicentric study", European Radiology, vol. 17, no. 11, pp. 2838-2844, 2007, this decrease in signal intensity difference between the blood-pool cavity and the (infarcted) myocardium leads to significantly less successful automatic segmentation of the ventricle.

An approach to improve a segmentation is to use information from other datasets acquired during the same MRI acquisition session (cardiac MRI scan) to assist the segmentation process. Multiple images of the same object, with each image containing specific properties of the object, can be used to assist other segmentation processes.

In this case, a plurality of additional datasets taken during the same imaging session in which the contrast-enhanced cine MRI was acquired, are able to visualize specific properties of the patient heart that can be used to assist ventricle segmentation at contrast-enhanced cine MRI dataset. For instance, delayed-enhancement MRI dataset is able to visualize myocardium infarct and first-pass perfusion MRI dataset is for instance able to visualize the dynamic of contrast liquid passage throughout the patient's myocardium.

FIG. 1 illustrates a typical example of MR datasets acquired at one MRI cardiac examination, a contrast-enhanced cine MRI (101) datasets along with various other datasets (102) acquired to visualize different properties of the patient heart, viability or also known as Delayed-enhancement imaging to assess myocardium infarct (102, top left image in FIG. 1), edema imaging to assess myocardial edema (102, top right image in FIG. 1), first-pass perfusion imaging to assess myocardium perfusion defects (102, bottom left image in FIG. 1) and T1 tissue mapping imaging to detect diffuse myocardium abnormalities (102, bottom right image in FIG. 1 in which the tissue relaxation times of the myocardium, after postprocessing, are superimposed on the acquired T1 MR mapped image).

Although the same object is being imaged, a certain property of the object may be more noticeable in one type of image while another property of the object in another type of image. By combining multiple properties obtained from different datasets, a better segmentation can be achieved.

WO2015/010745, "Multimodal Segmentation of Image Data", describes the use of a segmentation result from one dataset to assist in the segmentation of a second dataset. However, the datasets described by this prior art come from two different imaging modalities, e.g. x-ray angiography and MRI. It would however be advantageous to only have to rely on one modality to perform the examination. As this would be of less burden for the patient, less time consuming and cost less. Especially, it is the case with the magnetic resonance imaging modality where with only the matter of changing the imaging sequence parameters, different datasets with each their special features can be obtained. The idea of combining segmentations results between (contrast-enhanced) cine MRI dataset and other MRI dataset has been proposed for instance by Y. Lu, et al in "Automated quantification of myocardial infarction using graph cuts on contrast delayed enhanced magnetic resonance images", Quantitative Imaging in Medicine and Surgery, vol. 2, no. 2, pp. 81-86, 2012. They use their method to determine infarct area at delayed-enhancement MRI dataset with assistance from segmentation from cine MRI dataset.

J. Tufvesson, et al in "Automatic segmentation of myocardium at risk from contrast-enhanced SSFP CMR: validation against expert readers and SPECT", BMC Medical Imaging, vol. 16, no. 19, 2016 combine MR datasets to determine myocardial area at risk at contrast-enhanced cine MRI dataset of which the myocardial borders are already manually segmented with help from infarct segmentation from the delayed-enhancement dataset.

However, these methods do not attempt to segment the ventricle especially using contrast-enhanced cine MRI dataset.

SUMMARY

It is thus an object of embodiments herein to segment the ventricle on contrast-enhanced cine MRI datasets.

In accordance with embodiments herein, devices, computer program products and computer implemented methods are provided for delineating a ventricle from MRI data relating to the heart of a patient, the devices, program products and methods comprising, under control of one or more computer systems configured with specific executable instructions, a) providing (e.g., by obtaining from computer memory or acquiring by operation of an imaging device) a contrast-enhanced cine MRI dataset;

b) providing (e.g., by obtaining from computer memory or acquiring by operation of an imaging device) one or more additional MRI datasets;

c) segmenting one or more features on the additional MRI dataset or datasets;

d) mapping the segmented features to the contrast-enhanced cine MRI dataset; and e) using the segmented features as mapped in d) to assist segmentation of the ventricle on the contrast-enhanced cine MRI dataset.

The processing is generally applicable to various acquisition orientation of the datasets. However, it applies particularly but is not limited to datasets oriented according to short axis view of the heart.

In one exemplary embodiment, at least one of the said additional MRI datasets is a delayed-enhancement MRI dataset. Delayed-enhancement MRI dataset is acquired several minutes after contrast liquid administration. In this type of dataset, the infarcted region of the myocardium is highlighted. The information of the location and the range of infarct is then mapped into contrast-enhanced cine MRI dataset to assist the ventricle segmentation.

In another exemplary embodiment, at least one of the said additional MRI dataset is a first-pass perfusion MRI dataset. First-pass perfusion MRI dataset is able to visualize the passage of contrast liquid through the blood-circulation system and eventually through the body tissue. In this type of dataset, the blood pool cavities have the most dynamic signal intensity profile. The information of the location and the range of blood pool cavity is then mapped into contrast-enhanced cine MRI dataset to assist the ventricle segmentation.

In another exemplary embodiment, at least one of the said additional MRI dataset is a tissue mapping MRI dataset. In this type of dataset, various tissues may be characterized based on the exhibited relaxation time values. The information of the location and the range of these tissues is then mapped into contrast-enhanced cine MRI dataset to assist the ventricle segmentation.

In the case when there are more than one additional MRI dataset, it is possible to first perform a segmentation of a plurality of features at the first dataset, map the plurality of features to the second dataset, and then perform another segmentation of a plurality of features at the second dataset.

In an exemplary embodiment, the information collected from additional MRI datasets is used as seeds for segmentation at the contrast-enhanced cine MRI dataset.

In yet another exemplary embodiment, the information collected from additional MRI datasets is used to refine the already segmented ventricle in the contrast-enhanced cine MRI dataset.

Those who are skilled in the art will appreciate that when the additional MRI datasets are taken at the same imaging session the images will have approximately the same patient position.

According to embodiments herein, the information obtained from the additional MRI datasets is used to assist the ventricle segmentation at the contrast-enhanced MRI dataset at the cardiac phases that match the cardiac phase of the said plurality of additional MRI datasets.

Furthermore, the ventricle segmentation in the contrast-enhanced MRI dataset can be performed at all cardiac phases.

Embodiments also relate to a computer product directly loadable into the memory of a digital computer and comprising software code portions for performing the method according to embodiments herein when the product is run on a computer.

According to an aspect, embodiments relate to a MRI device for acquiring contrast enhanced two dimensional or three-dimensional sequences of image frames, the device comprising one or more acquisition modules for obtaining a plurality of image frames of the heart of a patient perfused by a contrast agent, such plurality of images being arranged to define a cine MRI dataset and one or more additional MRI datasets, the device further comprising a processor programmed to:

a) segment one or more features on the additional MRI dataset or datasets;

b) map the segmented features on the contrast-enhanced cine MRI dataset; and c) use the segmented features as mapped in b) to assist segmentation of the ventricle on the contrast-enhanced cine MRI dataset.

In an embodiment, the processor is programmed to segment the ventricle based on the contrast-enhanced cine MRI dataset and refine and/or correct said ventricle segmentation using the segmented features as mapped.

The images forming the additional MRI dataset or datasets are advantageously acquired during the same imaging session acquiring the images forming the contrast-enhanced cine MRI dataset to recover dead time inherent in this type of acquisition.

The additional MRI datasets may advantageously comprise one or more MRI datasets selected from the group consisting in: delayed-enhanced, first-pass perfusion, tissue mapping, viability, edema.

BRIEF DESCRIPTION OF THE DRAWINGS

The characteristics of the invention and the advantages derived therefrom will be more apparent from the following description of non-limiting embodiments, illustrated in the annexed drawings, in which.

DETAILED DESCRIPTION OF ILLUSTRATIVE EMBODIMENT(S)

A magnetic resonance imaging (MRI) apparatus comprises an imaging unit configured to carry out sequential imaging. The apparatus applies a radio-frequency magnetic field onto a subject (i.e. patient) placed in a static magnetic field. A magnetic resonance signal generated from the subject is detected due to the application of the radio-frequency magnetic field. Using the detected signals an image is created.

The magnetic resonance imaging apparatus also includes a gradient coil that adds spatial positional information to a magnetic resonance signal by applying a gradient magnetic field onto the subject.

Using different combinations of radiofrequency pulses and gradients, different MRI sequences can be made. An MRI pulse sequence is a programmed set of changing magnetic gradients. Different pulse sequences allow the radiologist to image the same tissue in various ways, and combinations of sequences reveal important diagnostic information.

Figure 2:
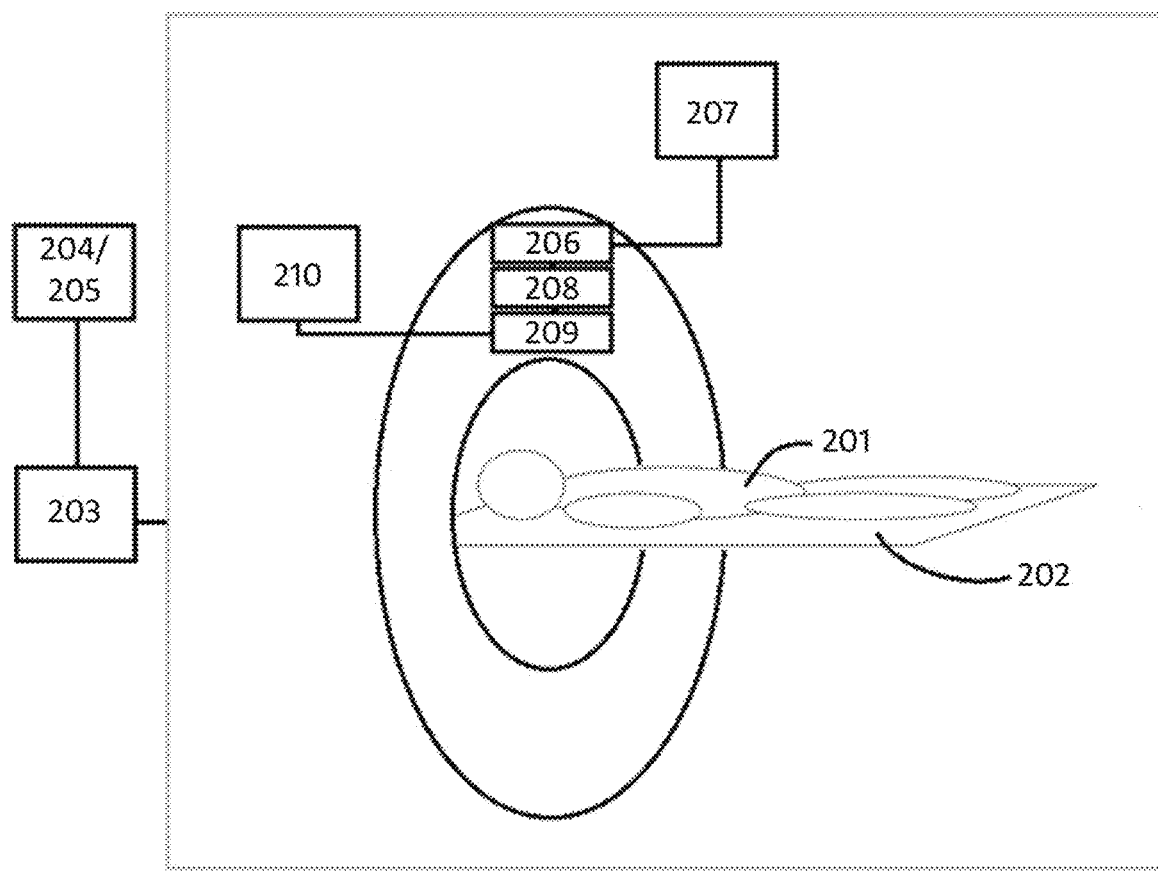
FIG. 2 illustrates an example of a high-level block diagram of an MR system.

FIG. 2 illustrates an example of a high-level block diagram of an MRI system.

Portions of the system (as defined by various functional blocks) may be implemented with dedicated hardware, analog and/or digital circuitry, and/or one or more processors operating program instructions stored in memory.

The MRI system of FIG. 2 includes an adjustable table 202 for a patient 201, a data processing module 203 and a magnet system 206.

The data processing module 203 includes one or more processors and memory that stores program instructions to direct the one or more processors to perform the operations described herein. The data processing module 203 also includes a display to present information to a user, such as the images, indicia, data and other information described herein and illustrated in the figures. The data processing module 203 also includes a user interface to receive inputs from the user in connection with operations herein, such as controlling operation of the imaging apparatus. For instance, scan parameters can be selected or altered, patient images may be displayed, and post-processing can be performed, including, for example, region of interest measurements, flow quantification and visual and/or quantitative control selecting projection perspectives to be used when obtaining complementary images and the like. The data processing module 203 may correspond to or include portions of one or more of the systems described within the patents and publications referenced herein and incorporated by reference.

One of the key aspects of an MRI system is the magnet system 206. The magnet system 206 generally comprises a large tube or a cylindrical magnet. The magnet is typically an electromagnet made from coils of superconducting wire typically helium cooled. The flow of electrical current through these coils produces a magnetic field. Permanent magnets can be used as well. The magnetic field has a certain field strength measured in Tesla. An important aspect of the magnet system 206 is the homogeneity of the magnetic field. That is a magnetic field that changes very little over the specified region or volume.

However, due to manufacturing imperfections or intervention room problems such as nearby steel posts, distortions of the magnetic field may arise. These inhomogeneities are corrected using a shim system 207. The corrections can either be performed manually or automatically. U.S. Pat. Nos. 6,252,402 and 7,332,912 disclose examples of shimming techniques for systems based on permanent magnets.

In clinical MRI hydrogen atoms of the human body are of importance. The nucleus of each hydrogen atom possesses spin also called nuclear spin angular momentum. That is, the nucleus of the hydrogen atom constantly rotates around an axis at a constant rate. When placed inside a magnetic field the nucleus the rotation axis tilts to align with the magnetic field.

The strong static magnetic field produced by the magnet system 206 aligns the spins of each hydrogen atom of the human body in a certain frequency that is dependent on the strength of the magnetic field.

Next, a radio frequency system 209 emits a radio frequency pulse (RF-pulse) towards the part of the body being examined, tuned to a specific range of frequencies at which hydrogen protons move. This results in some of the hydrogen protons being moved 180 degrees out of alignment with the static magnetic field and being forced into phase with other hydrogen protons.

The radio frequency system 209 generally comprises transmitting coils. The transmitting coil is usually built into the body of the scanner and transmits the RF-signal, generating an effective field perpendicular to the main magnetic field.

The energy which is absorbed by different hydrogen atoms in the body is then echoed or reflected back out of the body. The gradient system 208 is switched on and off to measure the echoes reflecting black out of the patient 201 and thus to localize the tissue signals.

Generally, a gradient system 208 consists of one or multiple gradient coils and gradient amplifiers.

Gradient coils are usually loops of wire or thin conductive sheets on a cylindrical shell lying just inside the bore of an MRI scanner. When current is passed through these coils a secondary magnetic field is created. This gradient field slightly distorts the main magnetic field in a predictable pattern, causing the resonance frequency of protons to vary as a function of position.

Typically, three sets of gradients are used: the x-, y- and z-gradients. Each coil set is driven by an independent power amplifier and creates a gradient field whose z-component varies linearly along the x-, y- and z-direction respectively producing the orthogonal field distortion required for imaging.

A data acquisition system 210 then receives the echoes. The data acquisition system 210 is responsible for measuring the signals from the protons and digitizing them for later post-processing. In general, the data acquisition system 210 consists of a coil, a pre-amplifier and a signal processing system.

The coil detects the induced voltage form the protons following an RF-pulse. The coil is tuned to the particular frequency of the returning signal.

The pre-amplifier is a low-noise high gain amplifier located inside the magnet room or the coil itself in order to be able to process the signals produced by the protons.

Furthermore, the signal processing system provides for instance further amplification of the signal, demodulation into kHz signal, low-pass filer, divided into real and imaginary parts then detected by the analog-to-digital converters (ADC). By applying an Inverse Fourier transformation (IFT) that converts the signal from the protons as mathematical data (k-space) into a picture that can be interpreted by the clinician.

The storage 204 is used to store the patient images that have been acquired immediately after they have been reconstructed. This is typically done in a universal language (vendor independent) such as DICOM. The storage can be a hard disk or a PACS (picture archiving and communications system) server 205 or a VNA (vendor neutral archive).

Figure 3:
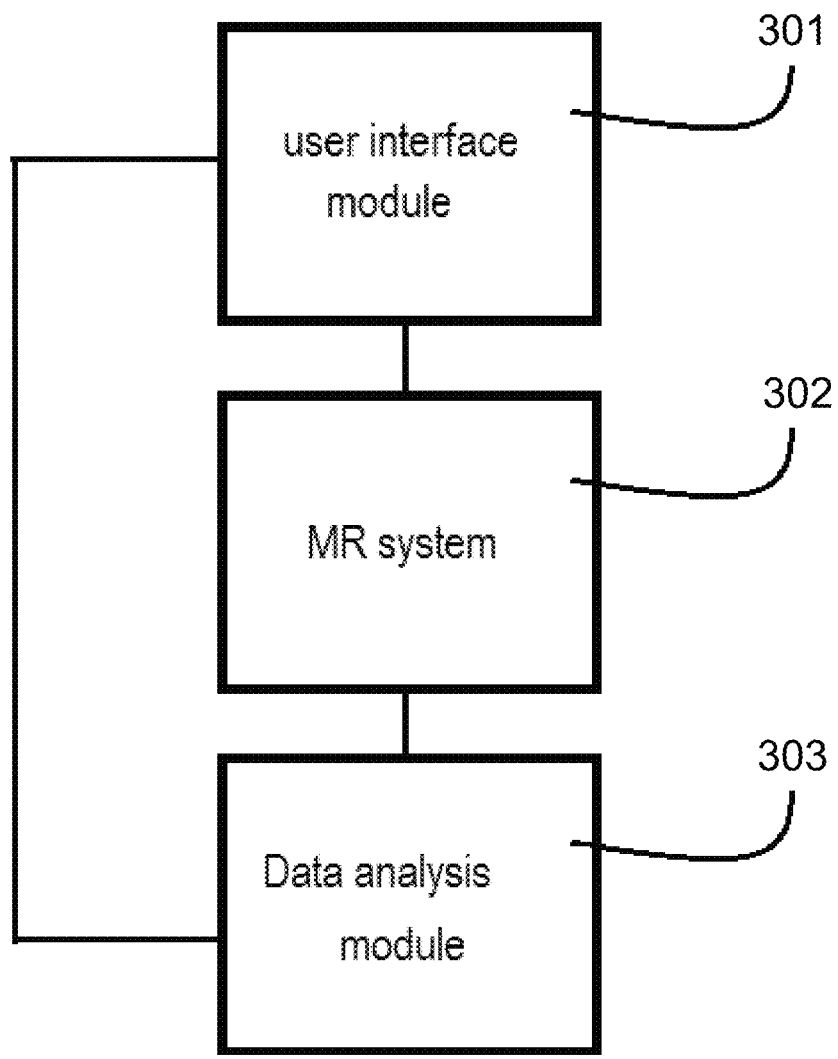
FIG. 3 is a functional block diagram of an exemplary MRI acquisition of a MR system in accordance with an embodiment herein.

FIG. 3 is a functional block diagram of an exemplary MRI acquisition in accordance to an embodiment herein which includes an MR system 302 that operates under commands from the user interface module and provide data to the data analysis module 303.

A clinician or other user acquires an MRI image of a patient 601 and stores this image on a hard disk 204 or a PACS or VNA server 205 in DICOM format.

Figure 1:
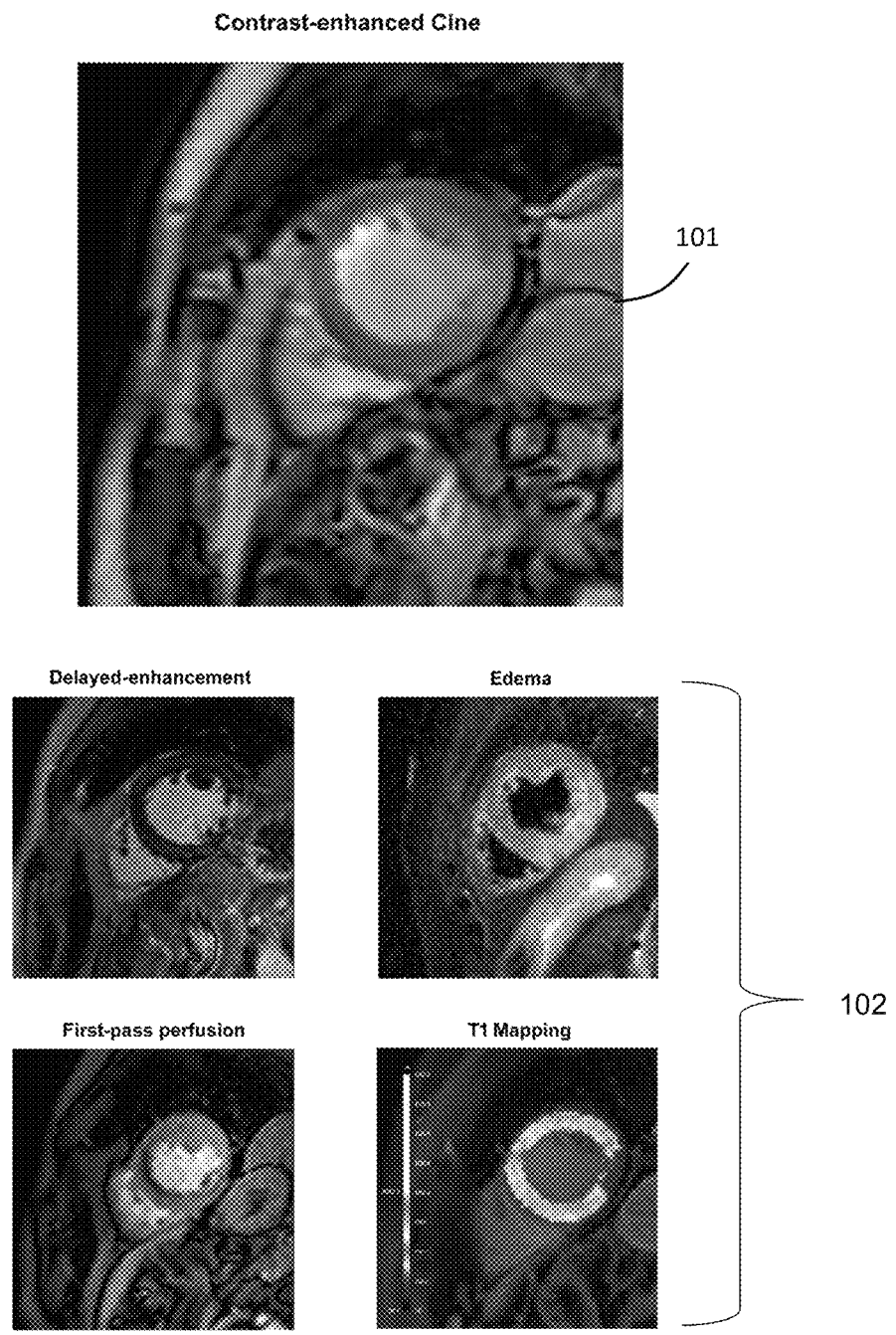
FIG. 1 shows an example of the contrast-enhanced cine MRI and the typical plurality of additional MRI datasets that were acquired at the same imaging session.

The MRI system 302 acquires MRI data of a volume of interest for instance the heart as shown in FIG. 1. The MR system typically includes a magnet system, a radio frequency system, a gradient system, a data acquisition system and a data storage.

The data analysis module 303 may be realized by a personal computer, workstation or other computer processing system that includes one or more processors. The data analysis module 303 processes the acquired data of the MRI system 302 to generate, for instance, cardiac analysis quantification.

The user interface module 301 interacts with the user and communicates with the data analysis module 303. The user interface module 301 can include different kinds of input and output devices, such as a display screen for visual output, a touch screen for touch input, a mouse pointer or other pointing device for input, a microphone for speech input, a speaker for audio output, a keyboard and/or keypad for input, etc.

An embodiment is implemented by the MR system of FIG. 2 as follows. A clinician or other user acquires an MR image of a patient 201 and stores this image on a hard disk 204 or a PACS server 205 in DICOM format.

The goal of the embodiment is to use additional datasets, acquired during a single cardiac MRI scan, to aid in ventricle segmentation on contrast-enhanced cine MRI datasets. A typical cardiac MRI examination (cardiac MRI scan) consist of several MRI acquisitions acquired during the same scan procedure to assess cardiac function. Such as:

Cine MR imaging for the assessment of cardiac function.
Tissue mapping, which includes T1, T2 and/or T2* mapping, for the assessment of detection of diffuse myocardium abnormalities.
Perfusion imaging for assessment of myocardium perfusion defects.
Viability imaging for the assessment of myocardium infarct. Either using late gadolinium enhancement MRI or black-blood late enhancement MRI.
Edema imaging (T2 weighted imaging) for the assessment of myocardium edema, such as due to an acute myocardium infarction.

Viability imaging is acquired approximately 15-20 minutes after injection of a gadolinium-based contrast agent, and nowadays this 'waiting time' is more frequently used to acquire the cine MRI (contrast-enhanced cine MRI). If the patient suffers from a myocardium infarct, enhancement of myocardium will occur, and enhancement of the infarcted myocardium within the contrast-enhanced cine MRI, resulting in inaccurate segmentation of the myocardium within contrast-enhanced cine MRI.

From segmentation point of view, the different MRI acquisition acquired during one cardiac examination contains complementary information allowing accurate segmentation of the myocardium within contrast-enhanced cine MRI. For instance, within perfusion the blood pool is displayed highly hyper-intense (high signal intensity), myocardium hypo-intense (low signal intensity) and myocardium perfusion defects slightly hyper-intense. Late gadolinium enhanced MRI results in a highly hyper-intense blood pool and infarcted myocardium whereas healthy myocardium is hypo-intense. Black-blood late enhancement MRI only infarcted myocardium is displayed hyper-intense, blood pool is highly hypo-intense and healthy myocardium slightly hypo-intense ("Dark blood late enhancement imaging", Peter Kellman et al., Journal of Cardiovascular Magnetic Resonance, 2016, 18:77). Within Edema MRI, the blood pool is very hypo-intense and the healthy myocardium slightly hyper-intense, whereas myocardium edema tissue is visualized hyper-intense. With respect to tissue mapping (T1, T2 and/or T2* mapping), this MRI acquisitions allows to compute the T1, T2 or T2* relaxation time within each pixel of the image and can for instance be calculated as taught by Ferreira et al, "Myocardial tissue characterization by magnetic resonance imaging: novel applications of T1 and T2 mapping", J Thorac Imaging. 2014 May; 29(3):147-54. MRI tissue mapping strategies offers an objective assessment of myocardial tissue properties. MRI tissue mapping refers to parametric maps that are generated from a series of images acquired with different T1 or T2 weighting so that each pixel can be assigned a T1 or T2 value. Each tissue type exhibits a characteristic range of normal T1 or T2 relaxation times at a particular field strength, deviation from which may be indicative of disease.

For the embodiment, it is therefore required to obtain a plurality of MRI datasets of the patient comprising of at least one contrast-enhanced cine MRI dataset (as shown in step 101 of FIG. 1) and one or more additional datasets (as shown in step 102 of FIG. 1), for instance first-pass perfusion, delayed-enhancement or tissue mapping datasets.

Figure 4:
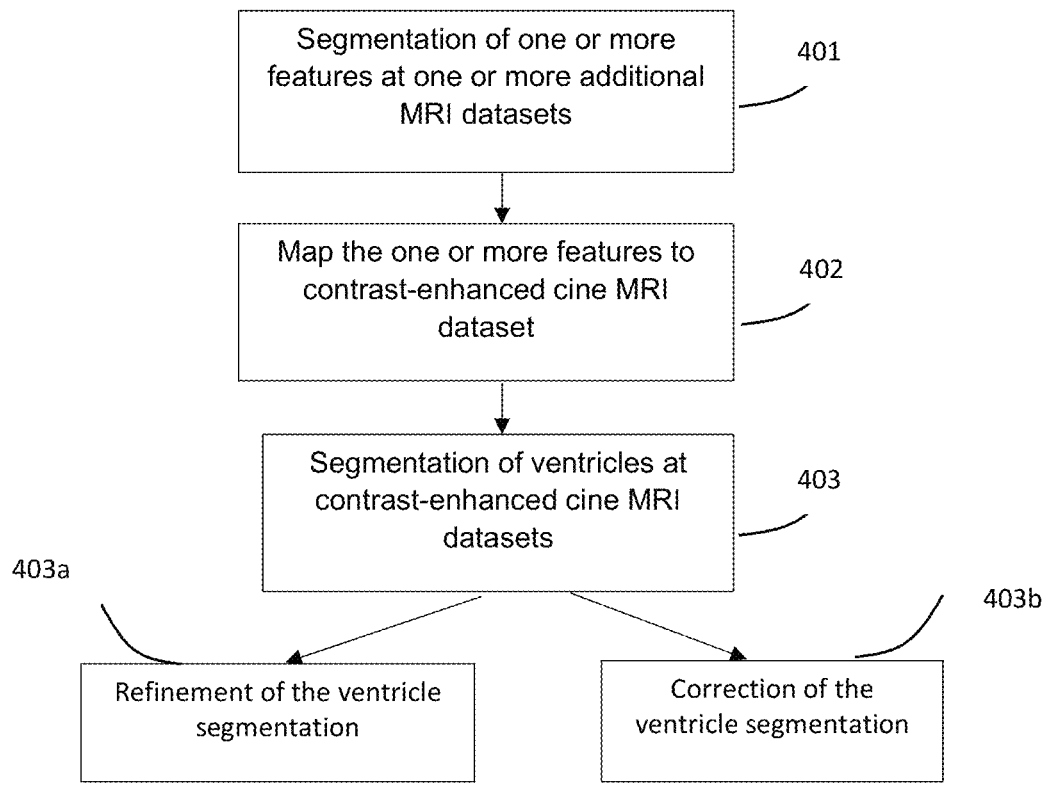
FIG. 4 shows an example of a flowchart for an exemplary embodiment.

FIG. 4 shows a flow chart illustrating the operations according to an embodiment herein.

The operations, typically performed by the data analysis module 303, can also be carried out by software code that is embodied in a computer product (for example, an optical disc or other form of persistent memory such as a USB drive or a network server). The software code can be directly loadable into the memory of a data processing system for carrying out the operations of FIG. 4.

Once MRI datasets have been obtained for the patient, at 401, the processing system performs a segmentation of one or more features in the one or more additional datasets. For instance, when the additional dataset is a first-pass perfusion MRI dataset, the blood-pool can be segmented as a feature. When for instance the additional dataset is a delayed enhancement MRI dataset, the myocardium infarct can be segmented as a feature. When for instance both first-pass perfusion MRI as well as delayed enhancement MRI datasets are available as additional datasets, both the blood-pool and the infarct can be segmented as features.

In an exemplary embodiment, ventricle segmentation is performed assisted by information obtained from for instance a first-pass perfusion MRI dataset taken at the same imaging session. A first-pass perfusion MRI dataset is a contrast-enhanced acquisition and it visualizes the passage of a contrast-solution throughout the blood circulation system, for instance throughout the heart chambers, and eventually throughout the tissues, for instance the myocardium.

A further detail of first-pass perfusion MRI dataset can be found in scientific literatures, for instance as taught by D. J. Atkinson, et al in "First-Pass Cardiac Perfusion: Evaluation with Ultrafast MR Imaging", Radiology, vol. 174, no. 3, pp. 757-762, 1990.

First-pass perfusion MRI dataset are typically taken at several slice locations across the heart. At each slice location, first-pass perfusion MRI dataset typically takes multiple images at a specific cardiac phase, over the course of several heartbeats while the patients hold their breath. Therefore, at a typical first-pass perfusion MRI dataset, at a specific slice location and over these multiple heart images, the heart does not appear to be moving.

What does appear in these multiple heart images when visualized sequentially, are the areas or image elements where the contrast solution passes, such as the blood-pool and the myocardium. These areas will increasingly appear to be bright and then gradually darken back to the initial brightness. This dynamic change in intensity is the strongest in the blood-pool as compared to the myocardium.

For this example (first-pass perfusion MRI as additional dataset), the feature that requires to be segmented in the additional dataset is the blood-pool. The segmentation of the blood-pool in the first-pass perfusion MRI dataset can for instance be done manually or (semi-)automatically. A fully automatic approach could for example be to localize areas in each frame of the first-pass perfusion dataset that have a high dynamic change in signal intensity. This allows to localize the blood cavities and blood-pool information such as for instance the endocardial contour can be obtained.

Methods to quantify this dynamic change in signal intensity include calculating of the standard deviation of signal intensities at each image elements over the multiple heart images taken at a specific slice location. Areas or image elements where the contrast solution passes will have a high signal intensity change and thus high standard deviation. Thus, from the original multiple heart first-pass perfusion images taken at a specific location, a new image can for instance be made of which each image element contains the standard deviation value of the signal intensities at the image element location over the multiple heart images. The next step would be to segment the image elements that have high standard deviation values.

An exemplary method can employ thresholding to segment the image elements. The thresholding method works by setting a certain value as a threshold, and any image element having a signal intensity above this threshold is marked as the object of interest, which is for instance the blood-pool. The threshold can for instance be set as taught by N. Otsu in "A Threshold Selection Method from Gray-Level Histograms", IEEE Transactions on Systems, Man, and Cybernetics, vol. SMC-9, no. 1, pp. 62-66, 1979.

In this method, a threshold value is calculated based on the image histogram, a table containing the occurrence frequency of each value. A threshold value is chosen to be a value that divides the histogram into two classes which are maximally separated and with each of the class to be as tight as possible. The final step is to group these image elements having values higher than the threshold and mark them as the desired feature (for instance the blood-pool), resulting in the segmented information from the first-pass perfusion MRI dataset.

Once the feature has been segmented in the additional dataset, in this case the blood-pool, at 402, the processing system maps the feature to the contrast-enhanced cine MRI dataset to aid in the ventricle segmentation in the contrast-enhanced MRI dataset.

For instance, when the additional dataset is a first-pass perfusion MRI dataset, the information available at one or more slices of first-pass perfusion as a result from the previous step is mapped into the corresponding slices at contrast-enhanced cine MRI dataset. For this, the destination slice at contrast-enhanced cine MRI dataset with the best matching properties first needs to be determined. This can be done for instance manually by the user or automatically as described below.

Figure 5:
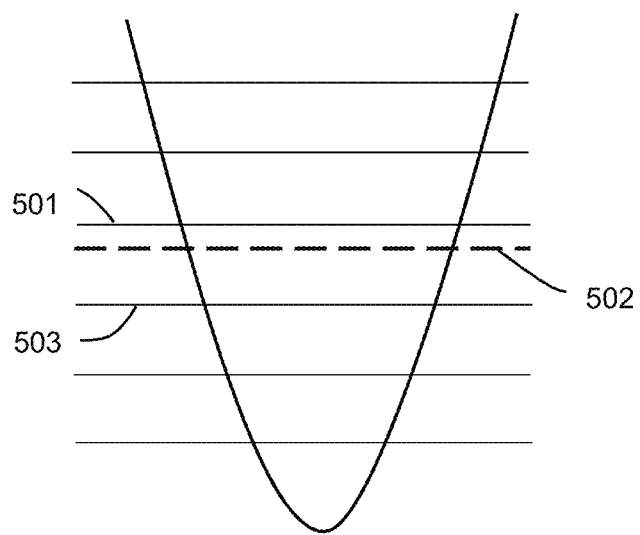
FIG. 5 shows an example of a method to match the slices from two different MRI datasets based on their slice locations.

The matching process is based on the location of and at which cardiac phase are the slices are acquired. By using the absolute system coordinates obtained from the MR system (through the "headers" of the conventional DICOM file format) it is possible to map objects from one MRI dataset to another MRI dataset. For this, a translation matrix can be defined as for instance taught in U.S. Pat. No. 7,864,997. FIG. 5 illustrates the matching process of slices of one dataset to slices of another dataset taken at the same imaging session, based on the slice location. Despite the fact that both datasets are taken at the same imaging session at approximately the same orientation, due to different area of interest in the acquisition planning, there is a possible position discrepancy between the slices of both datasets (see 501 and 503, versus 502).

Figure 6:
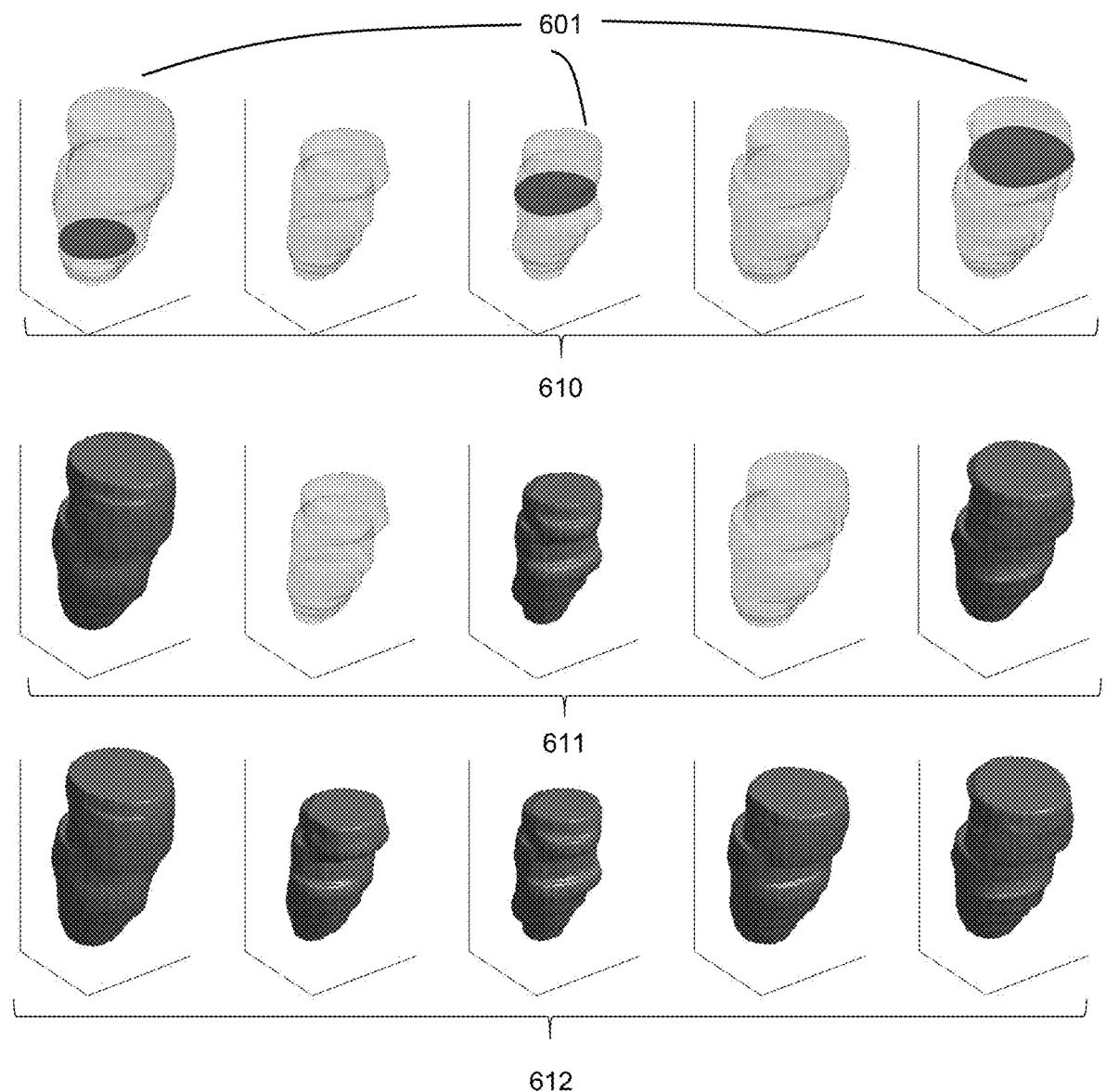
FIG. 6 shows an example of the segmentation process in a contrast-enhanced cine MRI dataset.

In FIG. 6, 602 is a slice from the additional dataset (in this example, first-pass MRI dataset) containing information to be mapped into the other dataset. One matching process for instance is to match the slices closest in position (502 is closer to 501 than to 503 in this case). After the best matching slices are found, the information can then be mapped, in the case presented by FIG. 5, from 502 to 501.

Matching slices based on their cardiac phase is required because different slice locations of first-pass perfusion MRI dataset may be taken at different cardiac phases. An exemplary method to match the cardiac phases of different slices is performed by matching their corresponding trigger time. It has been mentioned previously in this document that the MRI images are acquired at a certain cardiac phase.

As it is commonly known in the art that the heart beats at a certain rhythm, of which each beat is marked by the QRS wave of the electrocardiograph signal. Electrocardiograph is an electric signal produced by the beating heart. Trigger time is the amount of time that has lapsed since the R-wave. Thus, matching the trigger times of two MRI images will match the cardiac phase of the two MRI images. An exemplary method to map the information is simply by copying the information from the source slice to a destination slice that has a trigger time being closest to the source slice.

Optionally, slight patient motion between the acquired datasets can be corrected. For instance, between the first-pass perfusion dataset and the contrast-enhanced cine MRI. This can for instance be performed by image registration approaches such as introduced by F. Maes, et al in "Multi-modality Image Registration by Maximization of Mutual Information", IEEE Transactions on Medical Imaging, vol. 16, no. 2, pp. 187-198, 1997.

Once the feature has been mapped to the contrast-enhanced cine MRI dataset, at 503, the processing system performs the ventricle segmentation.

For instance, when the additional dataset is a first-pass perfusion MRI dataset, the blood-pool information has been mapped to the contrast enhanced cine MRI dataset.

FIG. 6 illustrates the 3D blood pool volumes over time, from the most left 3D volumes at end-diastolic phase of the heart where they are at their largest volumes, to the middle 3D volumes at end-systolic phase of the heart where they are at their smallest volumes, and to the rightest 3D volumes coming back to end-diastolic phase of the heart where they are almost at the largest volumes again.

From the results of the previous step, the blood pool cavity information is mapped into the specific slices of the cine MRI dataset that match the cardiac phases of the slices of the first-pass perfusion MRI dataset (see 3D volumes depicted at reference 601 of FIG. 6). Due to this, the blood pool cavity information is available not only on one specific cardiac phase but spread sparsely on different cardiac phases at the 4D cine MRI dataset (see the first row of reference 610 of FIG. 6, where some cardiac phases 601 contains the blood pool information from first-pass perfusion dataset and others do not).

The mapped information, which is in this example blood pool information, can then be used by the processing system at 403*a* to refine the segmentation methods for segmenting the ventricle.

An exemplary method to utilize the mapped information to segment the blood-pool in the contrast-enhanced cine MRI dataset is a seed-based segmentation. In a seed-based image segmentation, one or more image elements are specifically assigned as seed or a marker to the actual object to be segmented. Afterwards, the segmentation algorithm will classify each image element on the image whether it belongs to the object of interest based on their relation to the seed.

An exemplary seed-based segmentation method is a fuzzy-connected algorithm which is taught by J. K. Udupa and S. Samarasekera in "Fuzzy Connectedness and Object Definition: Theory, Algorithms, and Applications in Image Segmentation", Graphical Models and Image Processing, vol. 23, no. 3, pp. 246-261, 1996. Due to noise and image artefacts, boundaries between objects may not be so clear so that object segmentation might not be so accurate. However, the image elements that make up the object can be determined because they hang together, due to their similarity and adjacency.

In this method, the relations between image elements can be determined by calculating the so-called fuzzy relation or affinity. The degrees of affinity between image elements can be determined based on their adjacency and for instance their similarity in signal intensity values. This affinity level can be seen as a relationship strength between two image elements.

A series of adjacent image elements can be seen as a chain of which strength is determined by the weakest link. In this method, a chain or path from each image element to the seed is calculated along with the connection strength of those image elements to the seed.

One exemplary method to use the mapped blood pool information is to refine the calculation of the connection strength based on the characteristics of image elements contained within the mapped blood pool area.

Finally, the object can be segmented by setting a threshold of the strength, which will cut off the image elements which have lower strength than the threshold, leaving the image elements that have strong connectedness to the seed. Grouping these image elements together will constitute the final segmentation of the object.

Another exemplary method to utilize the mapped information to segment the blood-pool in the contrast-enhanced cine MRI dataset is refining the calculation of the connectedness strength threshold used to determine the final object based on the characteristics of image elements contained within the mapped blood pool area.

Another exemplary seed-based segmentation method to segment the blood pool is the well-known region growing method. The method started with an initial seed point(s) and classify the surrounding connected image elements as the final object based on one or more criteria, for example image elements having the similar signal intensity as the seed. An exemplary method to use the mapped blood pool information is to use it to determine the seed point or to refine the criteria used to determine whether connected image elements belong to the same object as the seed, for example by adjusting the signal intensity similarity measure.

Another exemplary segmentation method to utilize the mapped information to segment the blood-pool in the contrast-enhanced cine MRI dataset is a deformable model, with the mostly known example is the snake algorithm as introduced by M. Kass, et al in "Snakes: Active Contour Models", International Journal of Computer Vision, vol. 1, no. 4, pp 321-331, 1998. In this model, using an energy minimizing scheme, an initial contour is moved towards image features such as lines and edges, guided by external forces provided by the image and internal forces of the contour itself such as the rigidity and elasticity. Whereas the final contour will enclose the intended final object.

The first factor influencing the quality of the segmentation is the shape and form of the initial contour as a wrongly placed or sized initial contour may result in a false segmentation. Therefore, an exemplary method to use the mapped blood pool information is to use it as the initial contour. Alternatively, the mapped blood pool information is used to refine the initial contour. The second factor in the snake algorithm is the internal force of the contour. An exemplary method to use the mapped blood pool information is to use it to refine the internal force of the contour. As the mapped blood pool information holds the information of the correct blood pool lining, it can be used to adjust the desired rigidity and elasticity of the contour used to line the final blood pool information. The last factor in the snake algorithm is the external force. An exemplary method to use the mapped blood pool information is to use it to refine the external force acting on the moving contour.

Another exemplary segmentation method to utilize the mapped information to segment the blood-pool in the contrast-enhanced cine MRI dataset is model-based methods. In model-based methods, a model of the object to be segmented, often a statistical model, is built during a training phase based on a set of input data labelled as the object of interest. Based on this model, the object of interest on the test image is segmented by matching the model to the object present in the test image. One exemplary method of model-based methods is active appearance model, as introduced by: T. F. Cootes, et al in "Active Appearance Models", Proc. European Conference on Computer Vision 1998, vol. 2, pp. 484-198, 1998. This method uses a statistical appearance model of object to be segmented, which contains shape and signal intensity information of the object, which in this case the blood-pool. In contrast-enhanced cine, where the signal intensity of the blood pool differs less to the (infarcted) myocardium, the normal standard appearance model may not be adequate to accurately depict the blood pool. The mapped blood pool information may assist the segmentation by providing the specific information regarding the shape of the blood pool and the statistical signal intensity information based on signal intensities of the image elements enclosed by the mapped blood pool information, improving the statistical appearance model to depict the blood pool. With the updated model, the method may segment the blood pool more accurately.

The ventricle segmentation in the contrast-enhanced cine MRI dataset can be performed for instance in 3D or in 4D using the earlier obtained mapped blood-pool information.

For the 3D segmentation for instance, the segmentation is continued to segment the whole ventricle volume of that specific cardiac phase that contains the mapped blood-pool information from the first-pass perfusion MRI dataset (see second row of reference 611 of FIG. 6). This can be done for instance by extending the algorithm from working in 2D image to working in 3D volume. A 2D image can be seen as two-dimensional matrix of image elements, meanwhile 3D volume can be seen as a plurality of those 2D images stacked together. The extension of the segmentation from a 2D image to a 3D volume can for instance be performed simply by extending the concept of image elements neighborhood from 2D (image elements of the same image as neighbors) to 3D (image elements at adjacent image as neighbors). Another example is when the segmentation method is a deformable model method, instead of using a contour as the model, here a volume or a surface is used as a model to segment the blood pool.

Alternatively, for the 4D segmentation, the segmentation is continued to segment the whole ventricle volume of all cardiac phases, even if at those cardiac phases there is no mapped blood-pool information from the first-pass perfusion MRI dataset (see third row of reference 612 of FIG. 6). This can be done for instance by extending the fuzzy-connected algorithm from working in 2D image to working in 3D volume, and then to working in 4D space. A 4D space can be seen as multiple 3D volume but at different times, or this case at different cardiac phases. The extension of the segmentation from 3D volume to 4D space can for instance be performed simply by extending the concept of image elements neighborhood from 3D (image elements of the adjacent image as neighbors) to 4D (image elements at adjacent volume at adjacent cardiac phase as neighbors).

This results in a ventricle segmentation in a contrast-enhanced cine MRI dataset through the use of one or more additional datasets.

Optionally, delayed enhancement MRI can be used as an additional dataset. The delayed-enhancement MRI dataset is then used to assist the ventricle segmentation at contrast-enhanced cine MRI dataset. For this dataset, the feature to be segmented is for instance the infarct.

The first step is then the segmentation of the infarct at the delayed-enhancement MRI dataset. This can be done manually by the user or (semi-) automatically as described below.

At delayed-enhancement dataset, the infarcted myocardium tissue tends to appear brighter than the surrounding healthy myocardium due to its properties of contrast material retention as taught by A. C. van Rossum, et al in "Value of Gadolinium-Diethylene-Triamine Pentaacetic Acid Dynamics in Magnetic Resonance Imaging of Acute Myocardial Infarction with Occluded and Reperfused Coronary Arteries After Thrombolysis", The American Journal of Cardiology, vol. 65, no. 13, pp. 845-851, 1990. Using this property, the infarcted myocardium area can readily be selected by using any of the common thresholding methods.

The thresholding method works by setting a certain value as a threshold, and any image element having signal intensity above this threshold is marked as infarcted myocardium. The threshold value may be defined directly by the user or calculated semi-automatically by a certain algorithm, such as: the full-width at half maximum (FWHM) method as described by Amado, et al in "Accurate and Objective Infarct Sizing by Contrast-Enhanced Magnetic Resonance Imaging in a Canine Myocardial Infarction Model", Journal of the American College of Cardiology, vol. 44, no. 12, pp. 2383-2389, 2004. This method is started by the user selecting a point within the suspected area. An intermediate region of interest is formed by calculating group of image elements having signal intensities higher than 50% of the user selected point's signal intensity and still containing the user selected point.

The threshold for the infarct is set as 50% between the minimal and maximal signal intensity of this intermediate region. The final step of this step is to select groups of image elements that have signal intensities higher than the threshold and mark them as infarct.

Optionally fully automatic segmentation methods can be performed to extract the infarcted tissue. Fully automatic infarct segmentation on conventional delayed-enhancement dataset is hampered by the relatively low signal intensity difference between the blood-pool and the infarct as both have high signal intensity. For instance, when black-blood late enhancement MRI dataset is available, it can be used as an additional dataset. While infarct tissue still has high signal intensity, the blood-pool will appear very dark in this dataset. This increase in signal intensity difference will facilitate the automatic segmentation of the blood-pool, which in turn facilitate the fully automatic segmentation of the infarct.

The next step is to map the infarct information to contrast-enhanced cine MRI dataset. This step follows 402 of FIG. 4, as described previously, were the specific feature to be mapped is the infarct and the source dataset is delayed-enhancement MRI dataset. The infarct information contained in the slice of delayed-enhancement MRI dataset is mapped into a slice of contrast-enhanced cine MRI dataset which best matches the position (as illustrated by FIG. 5) and the cardiac phase.

After step 402, the infarct information is now available at the slice of contrast-enhanced cine MRI dataset that match both position and cardiac phase of the slice of delayed-enhancement MRI dataset. In this embodiment, the mapped infarct information will be used to aid in the segmentation of the ventricle in the contrast-enhanced cine MRI dataset.

Figure 7:
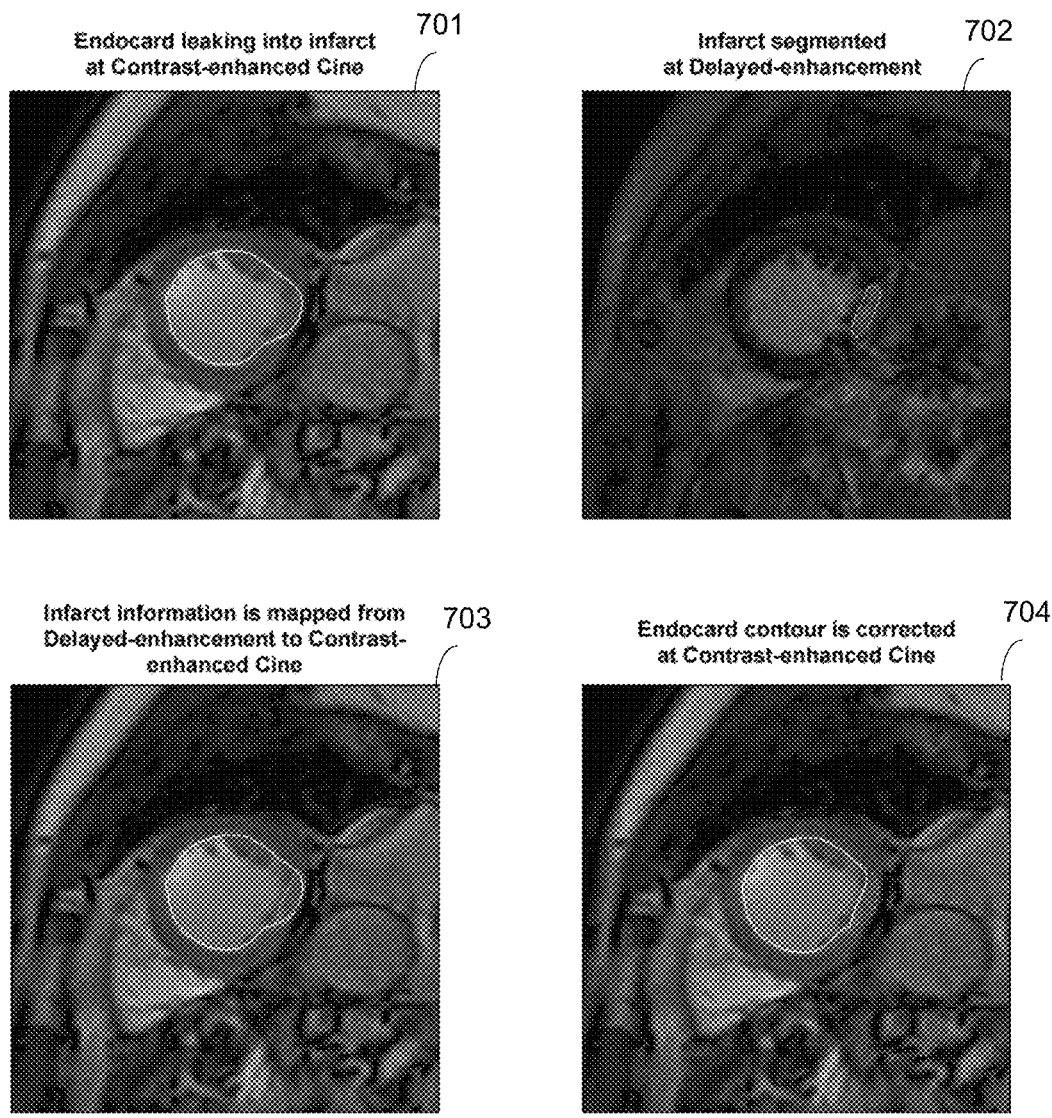
FIG. 7 shows an example of the utilization of mapped infarct information from a delayed-enhancement MRI dataset to correct a faulty blood-pool segmentation in a contrast-enhanced cine MRI dataset.

FIG. 7 illustrates an exemplary method to perform this task. Due to the fact that infarcted myocardial tissue appears to be bright within contrast-enhanced cine MRI due to its intake of contrast material and therefore the contrast between blood pool and the infarcted myocardial tissue become less, the endocardial segmentation may falsely leak into the infarct area (as can be seen in reference 701 of FIG. 7). Using the already segmented infarct segmentation of the delayed-enhancement MRI dataset (see reference 702 of FIG. 7) that is mapped into the contrast-enhanced cine MRI dataset, the faulty blood-pool segmentation can be refined (as described previously, see 403a of FIG. 4)

Alternatively, the mapped infarct information can for instance be used for correcting the mis-segmentation of the blood-pool (see 701 of FIG. 7). This step is reflected by operation 403b. One exemplary method to correct for this is by superimposing the mapped infarct information onto the already segmented but leaky ventricle area (see reference 703 of FIG. 7) and then subtracting the mapped infarct information from the already segmented ventricle area, leaving the final segmentation of the ventricle with only the blood-pool information, as illustrated by reference 704 of FIG. 7.

Figure 8:
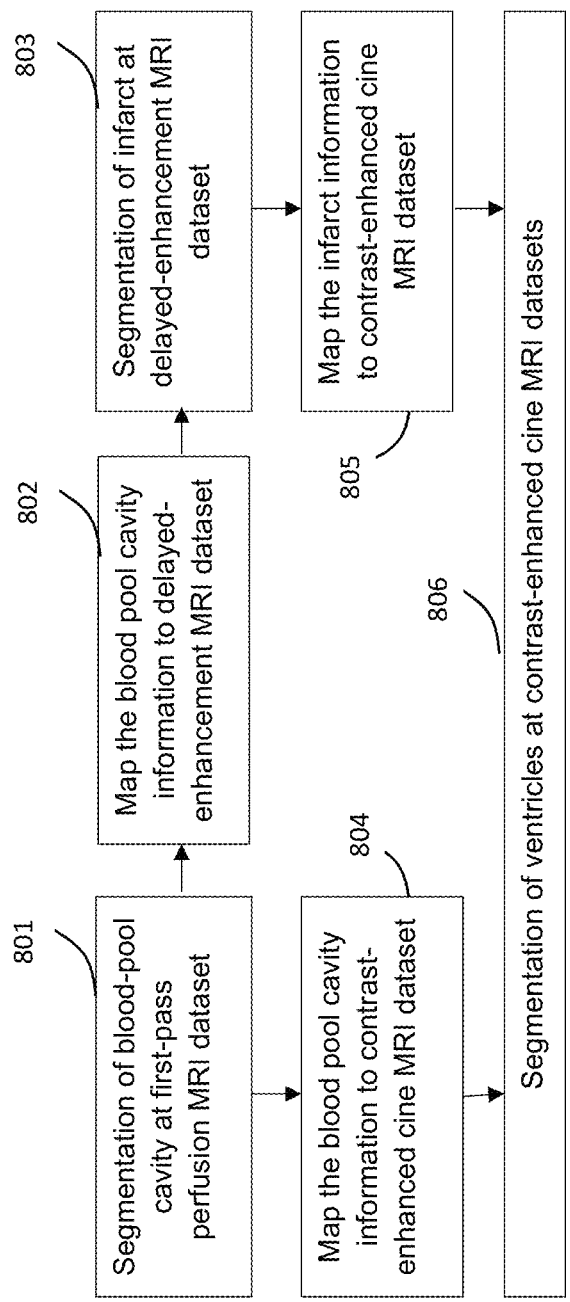
FIG. 8 shows an example of a method to utilize the information available at first-pass perfusion and delayed-enhancement MRI datasets taken at the same imaging session as contrast-enhanced MRI dataset to assist ventricle segmentation at contrast-enhanced cine MRI dataset.

Another exemplary embodiment is for instance the use of both first-pass perfusion MRI dataset and delayed-enhancement MRI dataset to assist the ventricle segmentation in contrast-enhanced cine MRI dataset as shown in FIG. 8. In this exemplary embodiment, the features to be segmented are the blood-pool and the infarct, for first-pass perfusion MRI dataset and delayed-enhancement MRI dataset, respectively.

The segmentation of the blood-pool in the first-pass perfusion MRI dataset (reference 801 of FIG. 8) can for instance be done manually by the user or (semi-) automatically as described.

After the blood-pool information has been obtained from the first-pass perfusion MRI dataset, it has to be mapped into the delayed-enhancement dataset (reference 802 of FIG. 8). The blood-pool information available on one or more slices of the first-pass perfusion MRI dataset is mapped to the corresponding best matching slices of the delayed-enhancement MRI dataset. The best matching slice is determined for instance based on the closest slice location and closest cardiac phase.

The mapped blood-pool information is used to assist the infarct segmentation in the delayed-enhancement MRI dataset. One exemplary method to utilize the mapped blood pool cavity information is by using it to segment the blood pool cavity at delayed enhancement MRI dataset, for instance by using it as a seed for the well-known region growing algorithm. This segmented blood pool cavity is then for instance used in combination with the thresholding method as described by earlier to segment the infarct at delayed-enhancement MRI dataset (reference 803 of FIG. 8). An alternative to the utilization of the mapped blood-pool information is to limit the infarct segmented as described earlier.

The blood-pool information that has been obtained at the first-pass perfusion is also mapped into the contrast-enhanced cine MRI dataset (see reference 804 of FIG. 8). The blood-pool information available on one or more slices of the first-pass perfusion MRI dataset is then mapped to the corresponding best matching slices at the contrast-enhanced cine MRI dataset. Best matching slice is determined for instance based on the closest slice location and closest cardiac phase.

The infarct information that has been obtained at the delayed-enhancement MRI dataset is also mapped into the contrast-enhanced cine MRI dataset (see reference 805 of FIG. 8) by determining the best matching slice for instance based on the closest slice location and closest cardiac phase.

Figure 9:
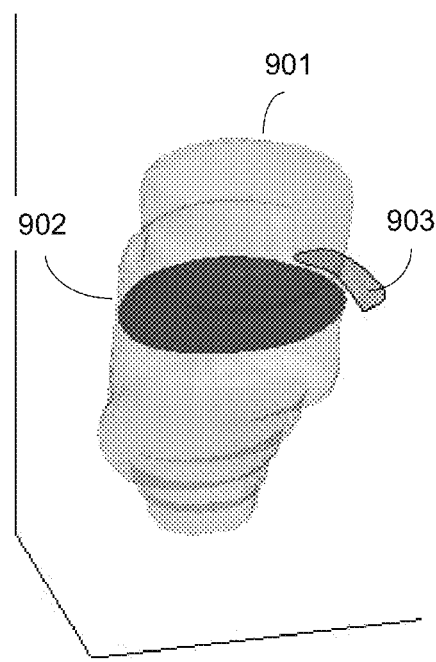
FIG. 9 shows an example of the availability of mapped blood-pool and infarct information in a contrast-enhanced cine MRI dataset.

FIG. 9 illustrates an example where the blood-pool information (902) from the first-pass perfusion MRI dataset and the infarct (903) information from the delayed-enhancement MRI dataset have been mapped into one of the slices of the contrast-enhanced cine MRI dataset, to segment the blood-pool volume (901) at the contrast-enhanced cine MRI dataset. However, since image slices of the first-pass perfusion MRI dataset and image slices of the delayed-enhancement MRI dataset are acquired at different positions and cardiac phases, the infarct information and the blood-pool cavity information may be available sparsely within the 4D cine dataset. In an exemplary embodiment, both information can be used for instance as seed for further segmentation.

For instance, a multi-seed segmentation method can be used to perform the segmentation. The aim of this method is to segment the image into several different objects. The method starts by first defining several objects that are to be segmented and then setting several image elements as a specific seed to the defined objects. For example, two types of objects, blood-pool and non-blood-pool objects, can be segmented. The seed for blood-pool object includes the mapped blood-pool information and the seed for non-blood-pool object includes the mapped infarct information.

After the seeds for different objects have been determined, the segmentation algorithm can classify for each image element to which object it belongs based on their relation to each type of seed. The advantage of a multi-seed segmentation is that it provides better border determination between two objects that have otherwise similar features.

In contrast-enhanced cine MRI dataset, the blood pool cavity and infarcted area both have similarly elevated signal intensity due to contrast-enhancement. This similarity in signal intensities may cause difficulty in determination of the borders between these two tissues. By placing a seed derived from the mapped blood-pool information on the blood-pool cavity and a seed derived from the mapped infarct information on the infarcted area, image elements surrounding these seeds can be better classified into blood-pool object and non-blood-pool objects which in turn improves border determination.

An exemplary method for multi-seeded image segmentation is taught by Gabor T. Herman and Bruno M. Carvalho in "Multiseeded Segmentation Using Fuzzy Connectedness", IEEE Transactions on Pattern Analysis and Machine Intelligence, vol. 23, no. 5, pp. 460-474, 2001.

In this method, several objects can be defined for example the blood-pool area and non-blood-pool area. For each defined object, seeds are defined. For each image element in the image, a connectedness strength to each seed type is calculated. The calculated connectedness strength value is similar to the one calculated by the fuzzy-connected method. However, it has a principal difference where in this method the membership of each image element to a certain object is not calculated by setting a threshold for the connected strength, but instead each image element is considered as belonging to one of the object of which it has the strongest membership and of which it is connected to.

Optionally a tissue mapping MRI dataset can be used as an additional dataset to assist in the ventricle segmentation in the contrast enhanced cine MRI dataset. Several features can be segmented in the tissue mapping MRI dataset, for instance blood-pool or myocardium. The corresponding relaxation times (T1, T2 and/or T2*) as obtained from tissue mapping MRI can be used to assist in the ventricle segmentation (as described previously. This feature information can also be combined with other additional datasets.

Another exemplary segmentation method to utilize information from addition MR sequences to segment the blood-pool in the contrast-enhanced cine MRI dataset the blood pool is machine learning algorithm. Machine learning is a subfield of computer science that "gives computers the ability to learn without being explicitly programmed". Evolved from the study of pattern recognition and computational learning theory in artificial intelligence, machine-learning explores the study and construction of algorithms that can learn from and make predictions on data—such algorithms overcome following strictly static program instructions by making data driven predictions or decisions, through building a model from sample inputs. Machine-learning is employed in a range of computing tasks where designing and programming explicit algorithms is infeasible.

Given a dataset of images with known class labels, machine-learning system can predict the class labels of new images. There are at least two parts to any such system. The first part of the machine-learning is a feature extraction (extractor), being an algorithm for creating a feature vector given an image. A feature vector comprises a series of factors (e.g. multiple numbers) that are measured or extracted from the image dataset(s), which describe or characterize the nature of the object of interest, in our case the left ventricle. These features are then used by the second part of the system, a classifier, to classify unseen feature vectors extracted from the unseen image. Given a (large) database of images and extracted feature vectors whose labels are known and were used beforehand to train the machine-learning algorithm, classifying unseen images based on the features extracted the same way as in images with (known) labels (training images) is possible. The development of ventricular cine MR segmentations methods is an ongoing endeavor, which has recently seen contributions from machine learning methods, as for instance thought by Tran P. V, "A fully convolutional neural network for cardiac segmentation in short axis MRI", arXiv preprint arXiv:1604.00494 (2016). An exemplary method to use the mapped blood pool information within a machine-learning algorithm is to expand the features vector with information of the myocardium infarct. Especially the relaxation values (T1, T2 and/or T2*) extracted from tissue mapping can be used to expand the feature vector and guiding the machine-learning algorithm of location and presents of myocardium infarct information. Segmented infarct from black-blood gadolinium MRI or late-gadolinium MRI can also be used to expand the feature vector.

There have been described and illustrated herein several embodiments of a method and apparatus for restoring missing information regarding the order and the flow direction of the velocity components. While particular embodiments of the invention have been described, it is not intended that the invention be limited thereto, as it is intended that the invention be as broad in scope as the art will allow and that the specification be read likewise. For example, the data processing operations can be performed offline on images stored in digital storage, such as a PACS or VNA commonly used in the medical imaging arts. It will therefore be appreciated by those skilled in the art that yet other modifications could be made to the provided invention without deviating from its spirit and scope as claimed.

The embodiments described herein may include a variety of data stores and other memory and storage media as discussed above. These can reside in a variety of locations, such as on a storage medium local to (and/or resident in) one or more of the computers or remote from any or all of the computers across the network. In a particular set of embodiments, the information may reside in a storage-area network ("SAN") familiar to those skilled in the art. Similarly, any necessary files for performing the functions attributed to the computers, servers or other network devices may be stored locally and/or remotely, as appropriate. Where a system includes computerized devices, each device can include hardware elements that may be electrically coupled via a bus, the elements including, for example, at least one central processing unit ("CPU" or "processor"), at least one input device (e.g., a mouse, keyboard, controller, touch screen or keypad) and at least one output device (e.g., a display device, printer or speaker). Such a system may also include one or more storage devices, such as disk drives, optical storage devices and solid-state storage devices such as random-access memory ("RAM") or read-only memory ("ROM"), as well as removable media devices, memory cards, flash cards, etc.

Such devices also can include a computer-readable storage media reader, a communications device (e.g., a modem, a network card (wireless or wired), an infrared communication device, etc.) and working memory as described above. The computer-readable storage media reader can be connected with, or configured to receive, a computer-readable storage medium, representing remote, local, fixed and/or removable storage devices as well as storage media for temporarily and/or more permanently containing, storing, transmitting and retrieving computer-readable information. The system and various devices also typically will include a number of software applications, modules, services or other elements located within at least one working memory device, including an operating system and application programs, such as a client application or web browser. It should be appreciated that alternate embodiments may have numerous variations from that described above. For example, customized hardware might also be used, and/or particular elements might be implemented in hardware, software (including portable software, such as applets) or both. Further, connection to other computing devices such as network input/output devices may be employed.

Various embodiments may further include receiving, sending, or storing instructions and/or data implemented in accordance with the foregoing description upon a computer-readable medium. Storage media and computer readable media for containing code, or portions of code, can include any appropriate media known or used in the art, including storage media and communication media, such as, but not limited to, volatile and non-volatile, removable and non-removable media implemented in any method or technology for storage and/or transmission of information such as computer readable instructions, data structures, program modules or other data, including RAM, ROM, Electrically Erasable Programmable Read-Only Memory ("EEPROM"), flash memory or other memory technology, Compact Disc Read-Only Memory ("CD-ROM"), digital versatile disk (DVD) or other optical storage, magnetic cassettes, magnetic tape, magnetic disk storage or other magnetic storage devices or any other medium which can be used to store the desired information and which can be accessed by the system device. Based on the disclosure and teachings provided herein, a person of ordinary skill in the art will appreciate other ways and/or methods to implement the various embodiments.

The specification and drawings are, accordingly, to be regarded in an illustrative rather than a restrictive sense. It will, however, be evident that various modifications and changes may be made thereunto without departing from the broader spirit and scope of the invention as set forth in the claims.

Other variations are within the spirit of the present disclosure. Thus, while the disclosed techniques are susceptible to various modifications and alternative constructions, certain illustrated embodiments thereof are shown in the drawings and have been described above in detail. It should be understood, however, that there is no intention to limit the invention to the specific form or forms disclosed, but on the contrary, the intention is to cover all modifications, alternative constructions and equivalents falling within the spirit and scope of the invention, as defined in the appended claims.

The use of the terms "a" and "an" and "the" and similar referents in the context of describing the disclosed embodiments (especially in the context of the following claims) are to be construed to cover both the singular and the plural, unless otherwise indicated herein or clearly contradicted by context. The terms "comprising," "having," "including" and "containing" are to be construed as open-ended terms (i.e., meaning "including, but not limited to,") unless otherwise noted. The term "connected," when unmodified and referring to physical connections, is to be construed as partly or wholly contained within, attached to or joined together, even if there is something intervening. Recitation of ranges of values herein are merely intended to serve as a shorthand method of referring individually to each separate value falling within the range, unless otherwise indicated herein and each separate value is incorporated into the specification as if it were individually recited herein. The use of the term "set" (e.g., "a set of items") or "subset" unless otherwise noted or contradicted by context, is to be construed as a nonempty collection comprising one or more members. Further, unless otherwise noted or contradicted by context, the term "subset" of a corresponding set does not necessarily denote a proper subset of the corresponding set, but the subset and the corresponding set may be equal.

Operations of processes described herein can be performed in any suitable order unless otherwise indicated herein or otherwise clearly contradicted by context. Processes described herein (or variations and/or combinations thereof) may be performed under the control of one or more computer systems configured with executable instructions and may be implemented as code (e.g., executable instructions, one or more computer programs or one or more applications) executing collectively on one or more processors, by hardware or combinations thereof. The code may be stored on a computer-readable storage medium, for example, in the form of a computer program comprising a plurality of instructions executable by one or more processors. The computer-readable storage medium may be non-transitory.

Preferred embodiments of this disclosure are described herein, including the best mode known to the inventors for carrying out the invention. Variations of those preferred embodiments may become apparent to those of ordinary skill in the art upon reading the foregoing description. The inventors expect skilled artisans to employ such variations as appropriate and the inventors intend for embodiments of the present disclosure to be practiced otherwise than as specifically described herein. Accordingly, the scope of the present disclosure includes all modifications and equivalents of the subject matter recited in the claims appended hereto as permitted by applicable law. Moreover, any combination of the above-described elements in all possible variations thereof is encompassed by the scope of the present disclosure unless otherwise indicated herein or otherwise clearly contradicted by context.

All references, including publications, patent applications and patents, cited herein are hereby incorporated by reference to the same extent as if each reference were individually and specifically indicated to be incorporated by reference and were set forth in its entirety herein.

The invention claimed is:

1. A method for delineating a ventricle from Mill data relating to the heart of a patient, the method comprising:
   a) providing a contrast-enhanced cine MRI dataset of the heart of the patient with the heart perfused by a contrast agent;
   b) providing at least one additional MRI dataset of the heart of the patient, wherein the at least one additional MM dataset is different from the contrast-enhanced cine Mill dataset;
   c) segmenting at least one feature of the at least one additional Mill dataset;
   d) mapping the at least one feature segmented in c) from the at least one additional dataset to the contrast-enhanced cine MRI dataset, wherein location information for the at least one feature is mapped from the at least one additional dataset to the contrast-enhanced cine Mill dataset; and
   e) segmenting the ventricle in the contrast-enhanced cine Mill dataset using the at least one feature mapped in d), wherein the segmenting uses the location information for the at least one feature as mapped in d).

2. A method according to claim 1, wherein:
the at least one additional Mill dataset comprises image data relating to a short axis view of the heart.

3. A method according to claim 1, wherein:
in e), the at least one feature mapped in d) is used as a seed for ventricle segmentation on the contrast-enhanced cine MM dataset.

4. A method according to claim 1, wherein:
in e), the at least one feature mapped in d) is used to refine or correct ventricle segmentation on the contrast-enhanced cine MM dataset.

5. A method according to claim 1, wherein:
the at least one additional MRI dataset comprises a delayed-enhancement MRI dataset.

6. A method according to claim 1, wherein:
the at least one additional MRI dataset comprises a first-pass perfusion MRI dataset.

7. A method according to claim 1, wherein:
the at least one additional MRI dataset of b) comprises a first-pass perfusion MM dataset and a delayed-enhanced MM dataset;
the segmenting of c) involves segmenting a blood-pool cavity on the first-pass perfusion MM dataset, mapping blood pool cavity information to the delayed-enhancement MRI dataset, and segmenting an infarct on the delayed-enhanced MRI dataset using the blood cavity information as mapped;
the mapping of d) involves mapping the blood pool cavity information to the contrast-enhanced cine MM dataset and mapping infarct information to the contrast-enhanced cine MRI dataset; and
the segmenting of e) involves segmenting the ventricle on the contrast-enhanced cine MRI dataset using the blood pool cavity information and the infarct information as mapped.

8. A method according to claim 1, wherein:
the at least one additional Mill dataset comprises a tissue mapping MM dataset.

9. A method according to claim 1, wherein the segmenting of c) involves segmenting a plurality of features in a plurality of additional MM datasets of the heart of the patient with the heart perfused by a contrast agent, wherein the plurality of additional Mill data sets are different from the contrast-enhanced cine MM dataset, wherein the plurality of features are segmented by:
segmenting a plurality of features on a first additional MM dataset of the plurality of additional Mill datasets;
mapping the plurality of features to a second additional Mill dataset of the plurality of additional MM datasets; and
segmenting a plurality of features on the second additional MM dataset of the plurality of additional Mill datasets.

10. A method according to claim 9, wherein:
the plurality of features segmented from the plurality of additional Mill datasets is mapped on the contrast-enhanced cine Mill dataset to obtain mapped segmented features; and
the mapped segmented features are used in e) to segment the ventricle in the contrast-enhanced cine Mill dataset.

11. A method according to claim 1, wherein:
the ventricle segmentation of e) is performed on the cardiac phase of the contrast-enhanced cine MM dataset matching the cardiac phase of the at least one additional MM dataset.

12. A method according to claim 1, wherein:
the ventricle segmentation of e) is performed on all cardiac phases of the contrast-enhanced cine MM.

13. A computer product directly loadable into the memory of a digital computer and comprising software code portions for performing the method according to claim 1 when the product is run on a computer.

14. An imaging device for acquiring contrast-enhanced two dimensional or three-dimensional sequences of image frames, the imaging device comprising one or more acquisition modules for obtaining a plurality of image frames of the heart of a patient, such plurality of images being arranged to define a cine Mill dataset of the heart of the patient with the heart perfused by the contrast agent and at least one additional MM dataset of the heart of the patient, wherein the imaging device further comprises a processor programmed to:
a) segment at least one feature of the at least one additional MM dataset;
b) map the at least one feature segmented in a) from the at least one additional dataset to the contrast-enhanced cine MM dataset, wherein location information for the at least one feature is mapped from the at least one additional dataset to the contrast-enhanced cine Mill dataset; and
c) segment the ventricle in the contrast-enhanced cine MM dataset using the at least one feature mapped in b), wherein the segmenting of the ventricle uses the location information for the at least one feature as mapped in b).

15. An imaging device according to claim 14, wherein the processor is further programmed to:
in c), use the at least one feature mapped in b) to refine or correct ventricle segmentation on the contrast-enhanced cine MM dataset.

16. An imaging device according to claim 14, wherein:
the images forming the at least one additional Mill dataset are acquired during the same imaging session that acquires the images forming the contrast-enhanced cine MM dataset.

17. An imaging device according to claim 14, wherein:
the at least one additional MRI dataset is selected from the group consisting of: a delayed-enhanced MRI dataset, a first-pass perfusion MM dataset, a tissue mapping MM dataset, a viability Mill dataset, and an edema Mill dataset.

18. An imaging device according to claim 14, wherein:
the mapping of b) involves matching slices of the at least one additional MM dataset to slices of the contrast-enhanced cine MM dataset based on slice location and cardiac phase at which the slices are acquired.

19. A method according to claim 1, wherein:
the mapping of d) involves matching slices of the at least one additional MM dataset to slices of the contrast-enhanced cine MM dataset based on slice location and cardiac phase at which the slices are acquired.

20. A method according to claim 1, wherein:
the at least one feature of c) includes location information that characterizes a blood pool cavity of the ventricle;
the mapping of d) maps the location information that characterizes the blood pool cavity of the ventricle from the at least one additional dataset to the contrast-enhanced cine Mill dataset; and
the segmenting of e) uses the location information that characterizes the blood pool cavity of the ventricle as mapped in d).

21. A method according to claim 20, wherein:
the at least one feature of c) further includes location information that characterizes an infarct of the ventricle;
the mapping of d) maps the location information that characterizes the infarct of the ventricle from the at least one additional dataset to the contrast-enhanced cine MM dataset; and the segmenting of e) uses the location information that characterizes the infarct of the ventricle as mapped in d).

22. A method according to claim 1, wherein:
the images forming the at least one additional Mill dataset are acquired during the same imaging session that acquires the images forming the contrast-enhanced cine MM dataset.

23. A method according to claim 1, wherein:
the at least one additional MRI dataset of the heart of the patient is acquired with the heart perfused by a contrast agent.

* * * * *